(12) United States Patent
Li et al.

(10) Patent No.: US 11,208,395 B2
(45) Date of Patent: *Dec. 28, 2021

(54) COMPOUND, LIQUID CRYSTAL MEDIUM CONTAINING THE COMPOUND AND APPLICATION THEREOF

(71) Applicant: SHIJIAZHUANG CHENGZHI YONGHUA DISPLAY MATERIAL CO., LTD., Hebei (CN)

(72) Inventors: Ming Li, Hebei (CN); Hongru Gao, Hebei (CN); Guoliang Yun, Hebei (CN); Xing Zhang, Hebei (CN); Jinsong Meng, Hebei (CN); Li Zhang, Hebei (CN); Lei Zhao, Hebei (CN); Yanli Dong, Hebei (CN)

(73) Assignee: SHIJIAZHUANG CHENGZHI YONGHUA DISPLAY MATERIAL CO., LTD., Hebei (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/473,978

(22) PCT Filed: May 8, 2018

(86) PCT No.: PCT/CN2018/085995
§ 371 (c)(1),
(2) Date: Jun. 26, 2019

(87) PCT Pub. No.: WO2019/033799
PCT Pub. Date: Feb. 21, 2019

(65) Prior Publication Data
US 2019/0345129 A1  Nov. 14, 2019

(30) Foreign Application Priority Data
Aug. 16, 2017  (CN) .......................... 201710701356.1

(51) Int. Cl.
| | | |
|---|---|---|
| *G02F 1/1333* | (2006.01) | |
| *C07D 333/76* | (2006.01) | |
| *C07D 409/04* | (2006.01) | |
| *C07D 409/06* | (2006.01) | |
| *C07D 409/12* | (2006.01) | |
| *C09K 19/06* | (2006.01) | |
| *C09K 19/30* | (2006.01) | |

(52) U.S. Cl.
CPC ......... *C07D 333/76* (2013.01); *C07D 409/04* (2013.01); *C07D 409/06* (2013.01); *C07D 409/12* (2013.01); *C09K 19/068* (2013.01); *C09K 19/3003* (2013.01); *C09K 19/3059* (2013.01); *C09K 19/3068* (2013.01); *C09K 2019/3004* (2013.01); *C09K 2019/3063* (2013.01); *C09K 2019/3071* (2013.01); *C09K 2019/3077* (2013.01); *C09K 2019/3078* (2013.01)

(58) Field of Classification Search
CPC .............. C09K 19/068; C09K 19/3003; C09K 19/3059; C09K 19/3068; C09K 2019/123; C09K 2019/3004; C09K 2019/3063; C09K 2019/3071; C09K 2019/3077; C09K 2019/3078; C07D 333/76; C07D 409/04; C07D 409/06; C07D 409/12
USPC ..................................... 252/299.61
See application file for complete search history.

(56) References Cited

U.S. PATENT DOCUMENTS

| | | | |
|---|---|---|---|
| 10,858,588 B2* | 12/2020 | Wang ................. | C09K 19/3491 |
| 2019/0078021 A1* | 3/2019 | Wang ..................... | G02F 1/137 |
| 2019/0345129 A1* | 11/2019 | Li ......................... | C07D 333/76 |

* cited by examiner

*Primary Examiner* — Geraldina Visconti
(74) *Attorney, Agent, or Firm* — Paratus Law Group, PLLC

(57) ABSTRACT

The present invention discloses a compound of which a structural formula thereof is represented as the following formula:

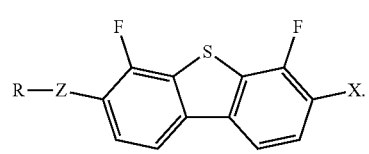

The compound disclosed by the present invention can be used as a liquid crystal compound and overcomes the problem that solubility of the traditional dibenzothiophene-class liquid crystals is poor, and thus can be better applied to the liquid crystal material field. The present invention further discloses a liquid crystal medium containing the compound and an application thereof.

11 Claims, 1 Drawing Sheet

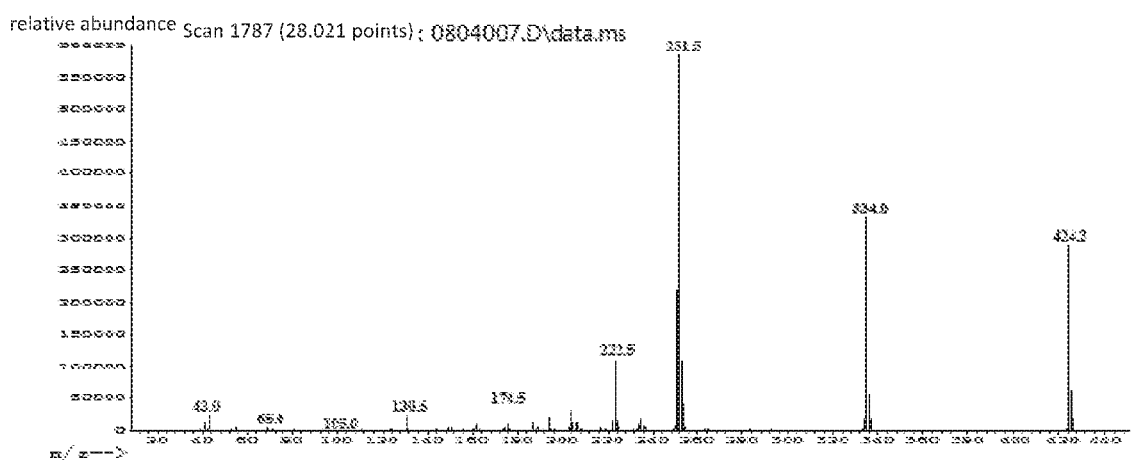

COMPOUND, LIQUID CRYSTAL MEDIUM CONTAINING THE COMPOUND AND APPLICATION THEREOF

CROSS REFERENCE TO PRIOR APPLICATION

This application is a National Stage Patent Application of PCT International Patent Application No. PCT/CN2018/085995 (filed on May 8, 2018) under 35 U.S.C. § 371, which claims priority to Japanese Patent Application No. 201710701356.1 (filed on Aug. 16, 2017), which are all hereby incorporated by reference in their entirety.

TECHNICAL FIELD

The present invention relates to the field of liquid crystal compound, and in particular to a compound, a liquid crystal medium containing the compound and an application thereof.

BACKGROUND ART

Since the Austrian scientist Reinitzer synthesized the liquid crystal for the first time in 1888, the liquid crystal industry has been really developing in recent 30 years. Because the liquid crystal display materials have obvious advantages, such as a low drive voltage, low power consumption, high reliability, lame display information amount, color display, non-flash, and capability of implementing panel display. Both the liquid crystal monomer and the liquid crystal display significantly develop. Currently, more than 10 thousand liquid crystal materials are synthesized by using the liquid crystal monomers. There are more than one thousand types of common liquid crystal materials, which, if classified according to the features of the central bridge bond and ring of the liquid crystal molecule, mainly include: diphenyl liquid crystal, cyclohexylbenzene liquid crystal, ester liquid crystal, alkyne, difluoromethoxy bridge, ethane, and heterocycle liquid crystals, and the like. The liquid crystal display further develops from the black-white small screen display with the twisted nematic (TN) mode or super twisted nematic (STN) modeused 30 years ago to the current color big screen display with the twisted nematic-thin film transistor (TN-TFT), vertical aligned-thin film transistor (VA-TFT), in-Plane Switching-thin film transistor (IPS-TFT), polymer dispersed liquid crystal (PDLC), and the like.

The new liquid crystal display modes mainly include: an optically compensated birefringence (OCB) mode, In-Plane Switching (IPS) liquid crystal display, a vertical alignment (VA) mode, an Axially Symmetric aligned Microcell (ASM) liquid crystal display, multi-domain twisted liquid crystal display, and the like.

The liquid crystal cells with various display modes have different designs and drive manners. The directions of the liquid crystal molecule director and the glass substrate are different. The liquid crystal molecule directors of the optically compensated birefringence (OCB) mode and the In-Plane Switching (IPS) liquid crystal display are parallel to the direction of the glass substrate, and the liquid crystal molecule directors of the vertical alignment (VA) mode and the Axially Symmetric aligned Microcell (ASM) liquid crystal display are perpendicular to the direction of the glass substrate in the non-electric field state.

For the IPS in the parallel arrangement manner, the dielectric anisotropy ($\Delta\varepsilon$) of the liquid crystal can be either positive or negative.

In the vertical alignment (VA) mode, all of the liquid crystal molecules are perpendicular to the direction of the glass substrate and parallel to the Vertical incident ray in the non-electric field. A good dark state may be displayed if the polarizers are orthogonal to each other, so that such device has good contrast with the dielectric anisotropy ($\Delta\varepsilon$) of the liquid crystal being necessarily negative. The optical anisotropy ($\Delta n$) of the liquid crystal, the thickness (d) of the liquid crystal cell, and the wavelength ($\lambda$) of the incident light impose hardly on effect on the contrast. The response time of the vertical alignment (VA) mode is significantly shorter than, which is about one half of, that of the twisted type device. Under the effect of the applied voltage, the VA device mainly generates bend deformation of the liquid crystal molecules, the electrically controlled birefringence (ECB) device generates splay deformation of the liquid crystal molecules, and the twisted display generates twist deformation of the liquid crystal molecules; and the response times thereof are inversely proportional to the bend, splay, and twist elastic constants. Generally, for most of the liquid crystals, the bend elastic constant is greater than the splay elastic constant, the splay elastic constant is further greater than the twist elastic constant, which is the reason why the response time of the VA device is relatively shorter.

For some existing structures similar to

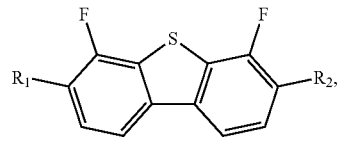

wherein $R_1$ and $R_2$ are respectively and independently selected from compounds of the chain alkyl group, the chain alkoxy group, and the like. Two fluorines at the lateral side and existence of the rigid structure dibenzothiophene in the molecules limit deflection between diphenyl rings, therefore, an absolute value of the dielectric anisotropy of this kind of compounds is relatively high and the birefringence thereof is extremely high. However, due to the existence of the rigid dibenzothiophene ring, this kind of alkylated liquid crystal compounds have a relatively low intersolubility and are easily crystallized in low temperature.

Therefore, a new liquid crystal compound needs to be provided and further applied to the display device, so that the performance of the display device can be more close to the idealization.

SUMMARY OF THE INVENTION

In order to solve the above-mentioned technical problem, the first objective of the present invention is to provide a compound.

The second objective of the present invention is to provide a liquid crystal medium.

The third objective of the present invention is to provide an application of the liquid crystal medium in preparation of a liquid crystal mixture, a material for a liquid crystal display device, or a material for an electro-optical display device.

In order to achieve the above-mentioned first objective, the present invention adopts the following technical solution:

A compound, a structural formula of the compound being represented as the following formula I:

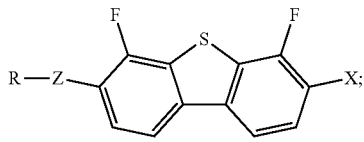

wherein:

R represents one of cyclopropyl group, cyclopentyl group, and 2-tetrahydrofuryl group;

Z represents one of a single bond, $-CH_2-$, $-O-$, $-CH_2CH_2-$, $-CH_2O-$, $-CF_2O-$, and $-COO-$; and X represents one of H, F, an alkyl group having 1-7 carbon atoms, and an alkoxy group having 1-7 carbon atoms, wherein in the alkyl group having 1-7 carbon atoms and the alkoxy group having 1-7 carbon atoms, one or more H atoms can be substituted by F.

In the present invention, a structural formula of the 2-tetrahydrofuryl group is:

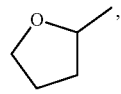

wherein " ----- " connected to C neighboring to O represents a single bond.

Preferably, the structural formula of the compound of which the structural formula is formula 1 is specifically represented as the following formulas I1 to I17:

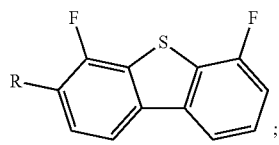

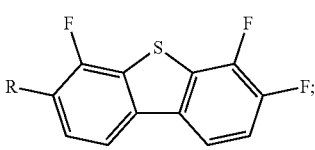

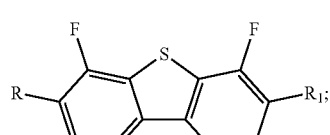

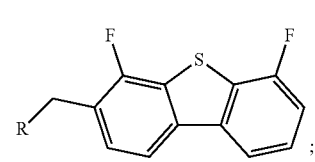

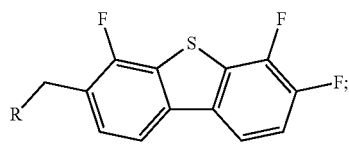

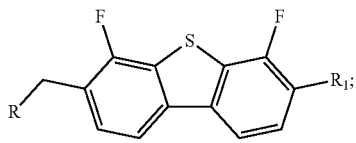

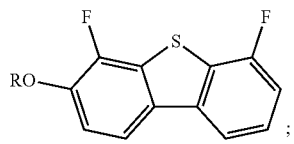

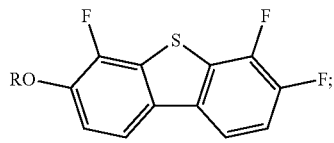

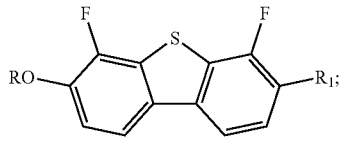

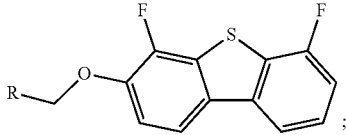

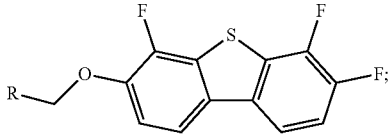

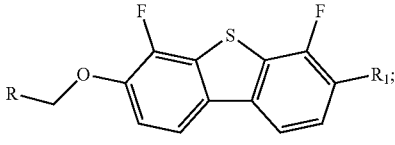

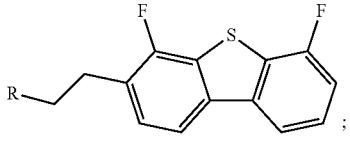

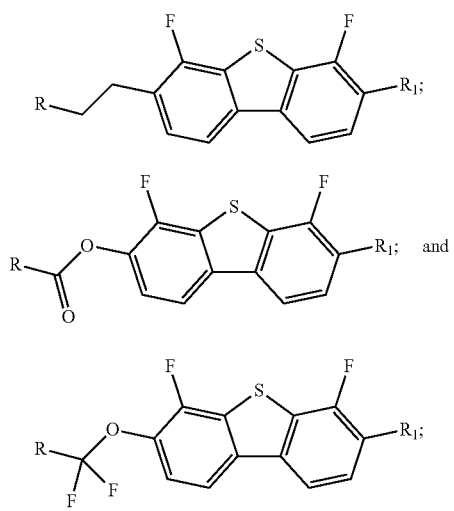

wherein:

R represents one of cyclopropyl group, cyclopentyl group, and 2-tetrahydrofuryl group; and R₁ represents an alkyl group having 1-7 carbon atoms or an alkoxy group having 1-7 carbon atoms, in which one or more H atoms can be substituted by F.

Preferably, the structural formula of the compound of which the structural formula is formula I is specifically represented as the following formulas I1-1 to I17-1:

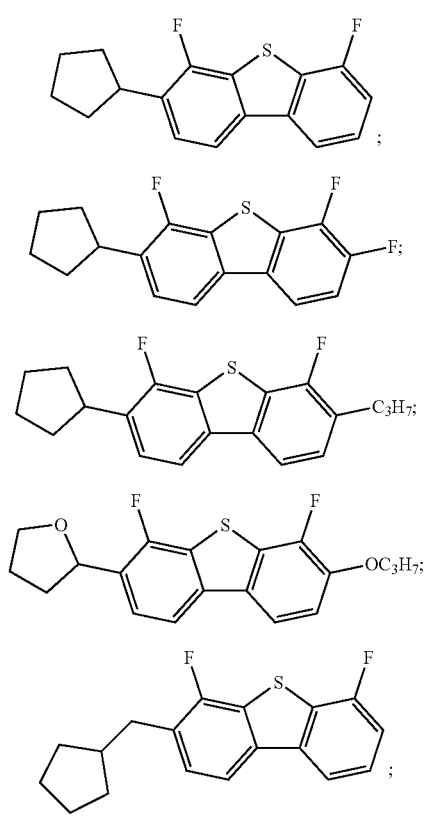

-continued

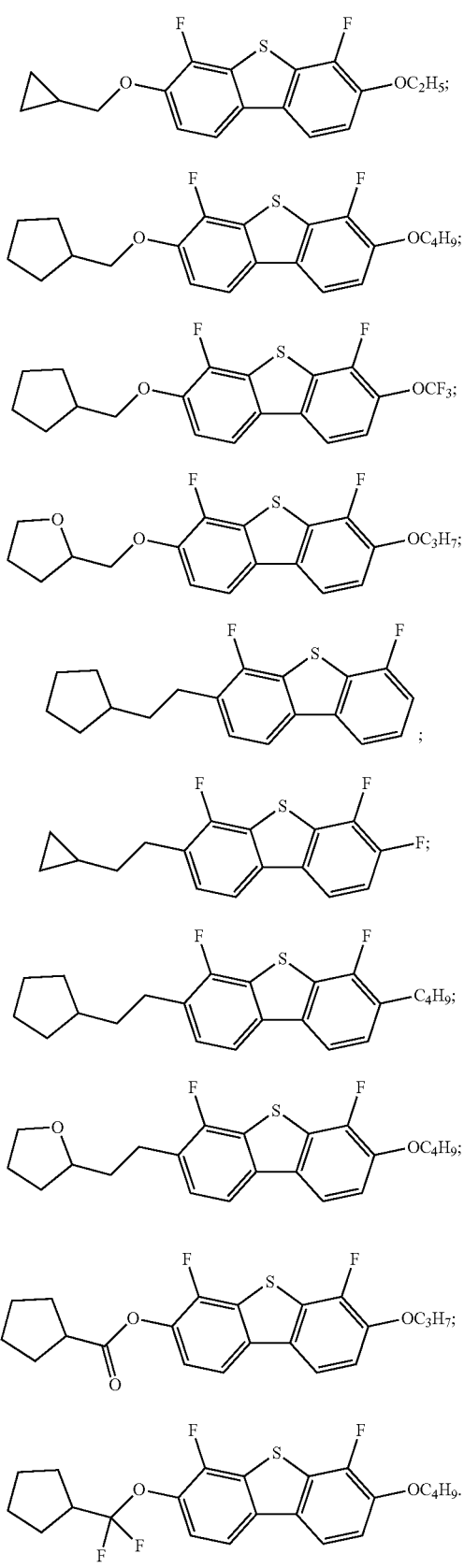

Preferably, in the present invention, the compound of which the structural formula is formula I can be synthesized by using a synthetic route comprising but not limited to the following synthetic route:

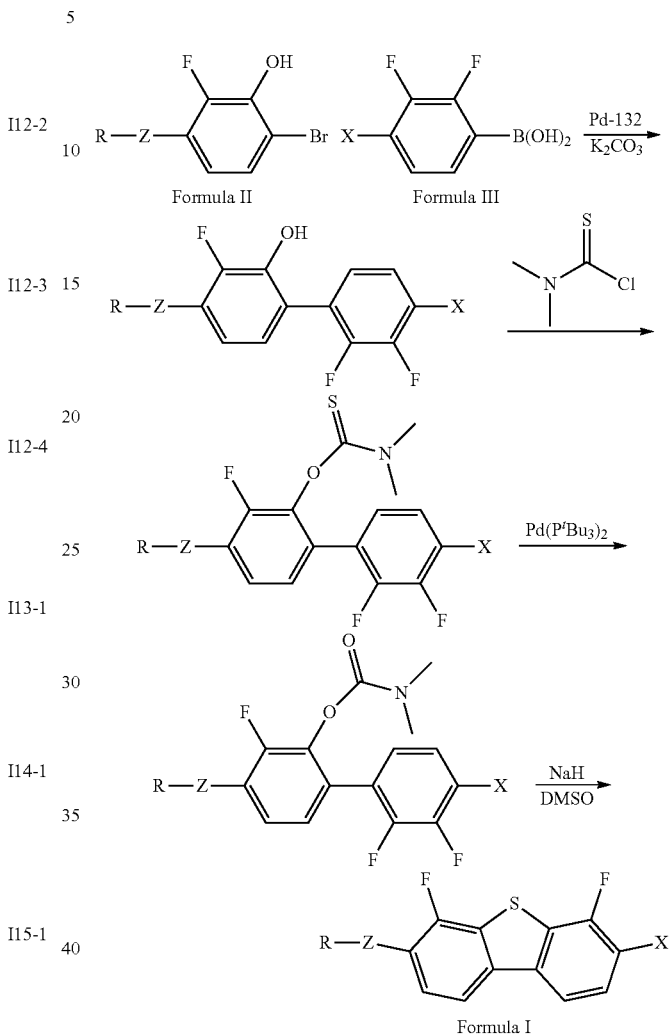

According to the above-mentioned synthetic route, compounds of formula II and formula III are key intermediates for synthesizing the target compound, that is, the compound of formula I.

Formula II:

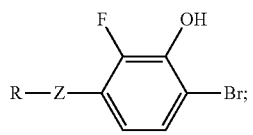

formula III:

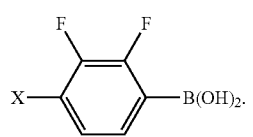

The key intermediates: the compounds of formula II and formula III for synthesizing the compound represented by formula I can be obtained via a commercial approach, or can be prepared with reference to a synthetic method of a similar compound in the following documents: *Org. Biomol. Chem.,* January 2003, 1609-1624, and EP2399896. An principle, an operation process, a conventional post-process, silica column chromatography, and recrystallization purification of such the method are well known to a person skilled at synthesis in the art, and the synthetic process thus can be necessarily implemented to obtain the target compound.

All reactions of all steps of all of the above-described methods are performed in solvents. The solvents are selected from at least one of tetrahydrofuran, N,N-dimethyl formamide, ethyl alcohol, methyl alcohol, dichloromethane, acetone, methylbenzene, and deionized water.

In order to achieve the second objective, the present invention provides a liquid crystal medium, wherein the liquid crystal medium contains one or more of the compounds of which structural formula is formula I.

Preferably, the liquid crystal medium further contains one or more compounds, which serve as second component, of which a structural formula thereof is formula IV:

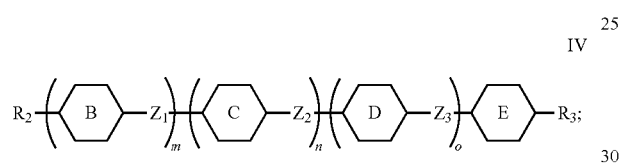

IV wherein:

$R_2$ and $R_3$ respectively and independently represent any one group in the following groups represented by (1)-(3):

(1) a linear alkyl group having 1-7 carbon atoms or a linear alkoxy group having 1-7 carbon atoms;

(2) a group formed by substituting —O—, —COO—, —OOC—, or —CH=CH— for one or more —CH$_2$— in any one group represented by (1); and (3) a group formed by substituting F, Cl, —CH=CH$_2$, or —CH=CH—CH$_3$ for one or more H atoms in any one group represented by (1);

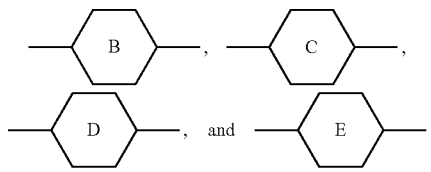

respectively and independently represent any group in the following groups:

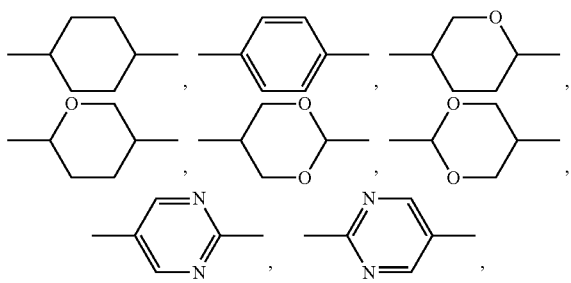

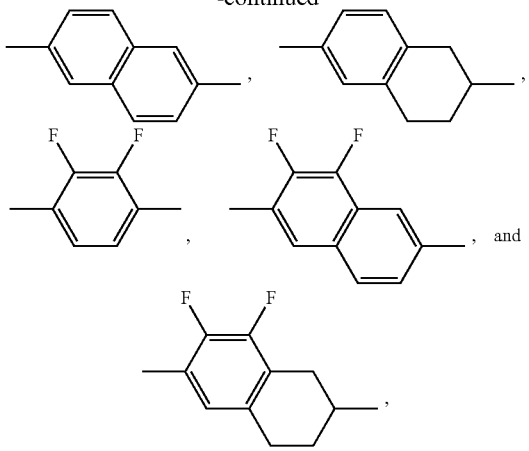

wherein at least one of

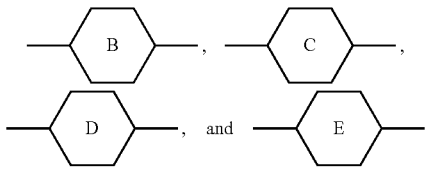

is selected from one of

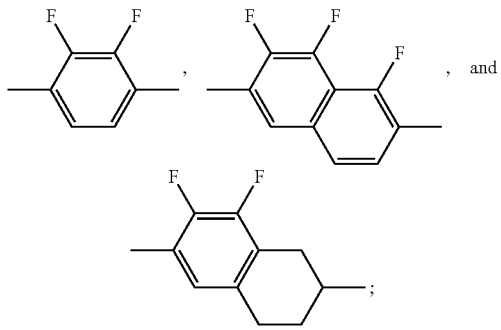

m, n, and o respectively and independently represent 0 or 1; and $Z_1$, $Z_2$, and $Z_3$ respectively and independently represent one of a single bond, —C$_2$H$_4$—, —CH=CH—, —C≡C—, —COO—, —OOC—, —CH$_2$O—, —OCH$_2$—, —CF$_2$O—, and —OCF$_2$—, in which any H atom can be substituted by F.

Preferably, the liquid crystal medium further contains one or more compounds of which structural formula thereof is formula V:

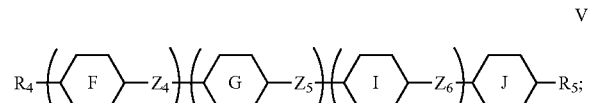

V wherein:

$R_4$ and $R_5$ respectively and independently represent an alkyl group having 1-10 carbon atoms or an alkenyl group having 2-10 carbon atoms, in which any —CH$_2$— can be substituted by —CH$_2$O—, —OCH$_2$—, or —C≡C—, and any H atom can be substituted by F;

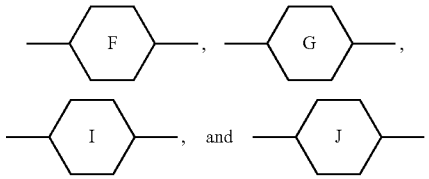

respectively and independently represent the following groups:

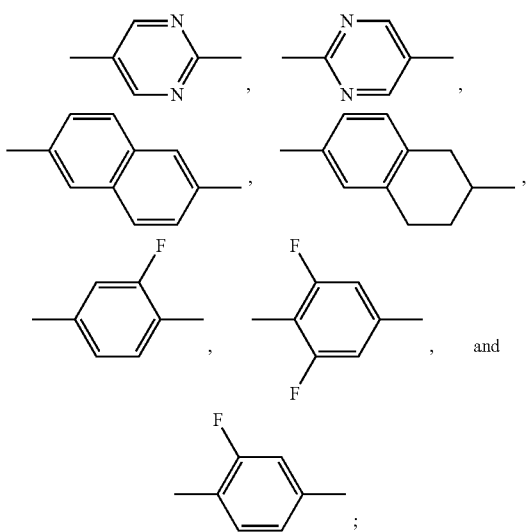

p, q, and r respectively and independently represent 0 or 1; and

Z$_4$, Z$_5$, and Z$_6$ respectively and independently represent one of a single bond, —C$_2$H$_4$—, —CH═CH—, ≡ , —COO—, —OOC—, —CH$_2$O—, —OCH$_2$—, —CF$_2$O—, and —OCF$_2$—, in which any H atom can be substituted by F.

Preferably, in the liquid crystal medium, a mass percentage of the compound of which the structural formula is formula I is 1-24%, a mass percentage of the compound of which the structural formula is formula IV is 35-58%, and a mass percentage of the compound of which the structural formula is formula V is 30-46%.

Preferably, the structural formula of the compound of which the structural formula is formula IV is specifically represented as the following formulas IV1 to IV15:

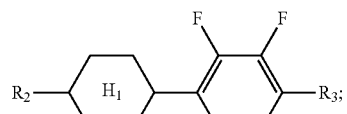

IV1

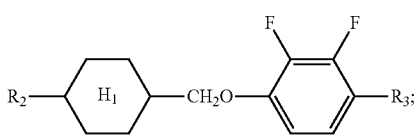

IV2

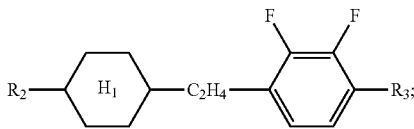

IV3

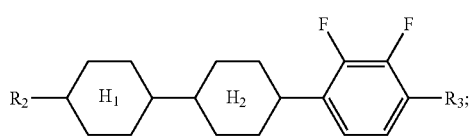

IV4

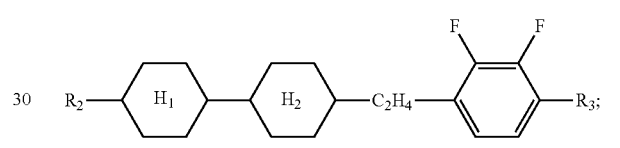

IV5

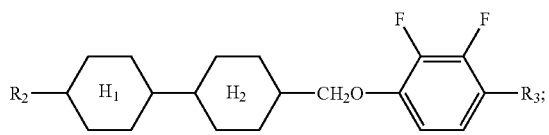

IV6

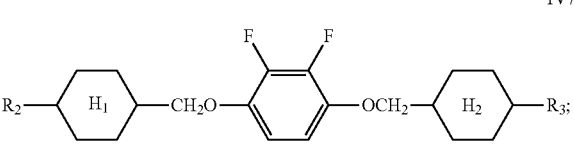

IV7

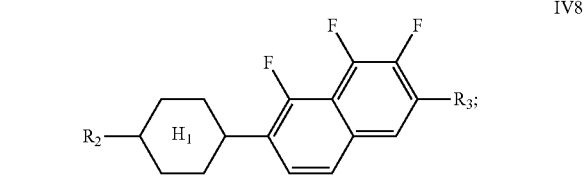

IV8

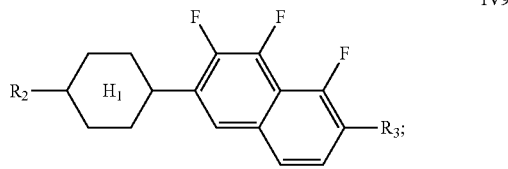

IV9

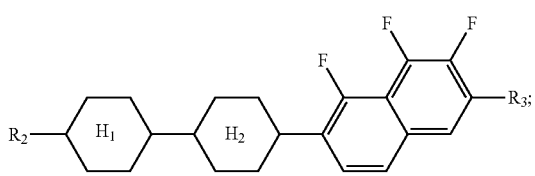

IV10

-continued

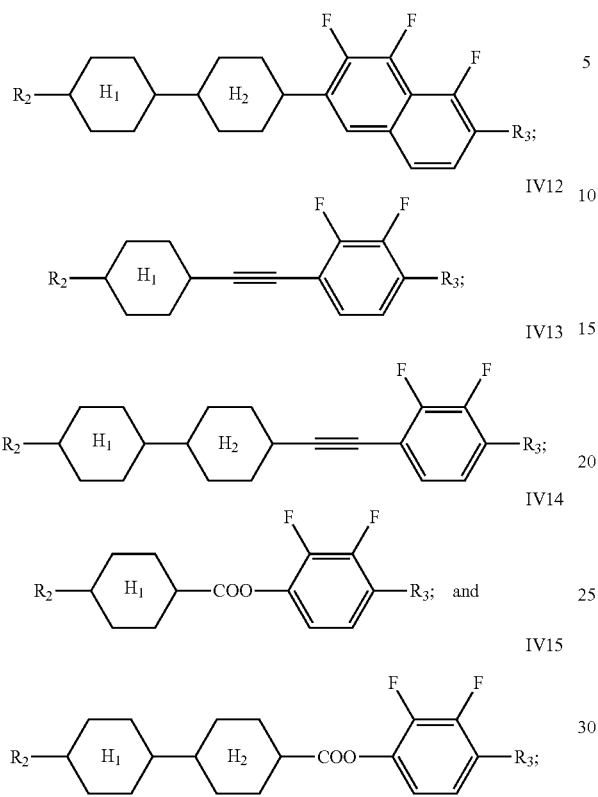

wherein:
R$_2$ and R$_3$ respectively and independently represent any one group in the following groups represented by (1)-(3):
(1) a linear alkyl group having 1-7 carbon atoms or a linear alkoxy group having 1-7 carbon atoms;
(2) a group formed by substituting —O—, —COO—, —OOC—, or —CH=CH— for one or more —CH$_2$— in any one group represented by (1); and
(3) a group formed by substituting F, Cl, —CH=CH$_2$, or —CH=CH—CH$_3$ for one or more H atoms in any one group represented by (1);

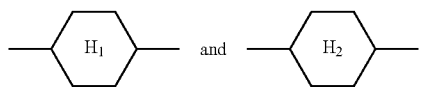

respectively and independently represent any group in the following groups:

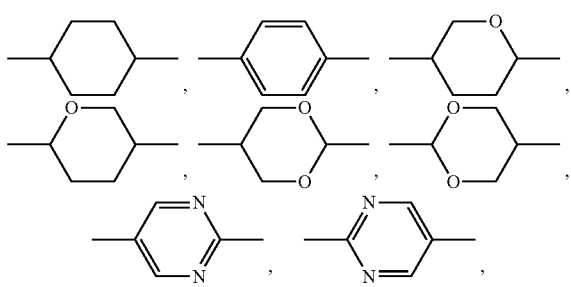

-continued

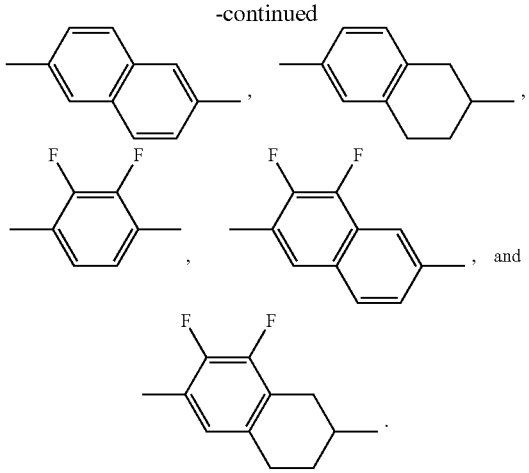

Preferably, the structural formula of the compound of which the structural formula is formula V is specifically represented as the following formulas V1 to V16:

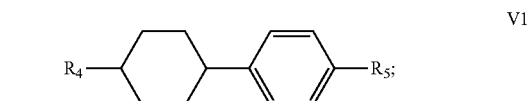
V1

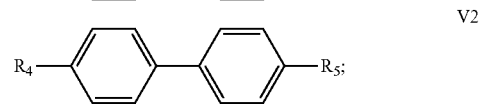
V2

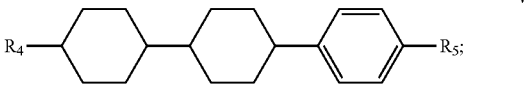
V3

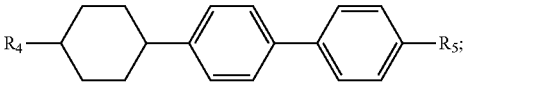
V4

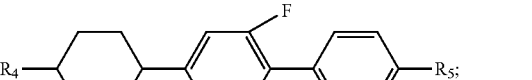
V5

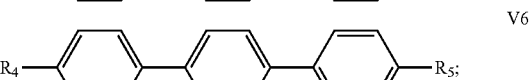
V6

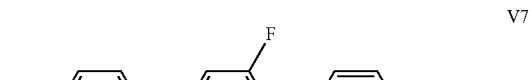
V7

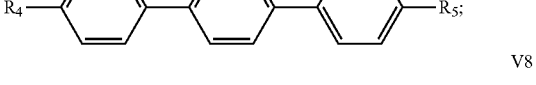
V8

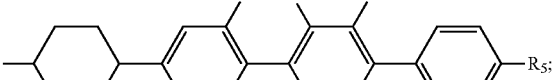
V9

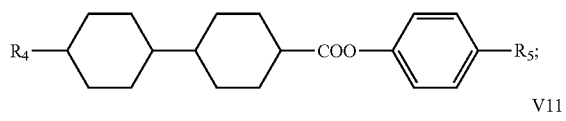
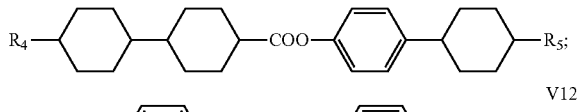
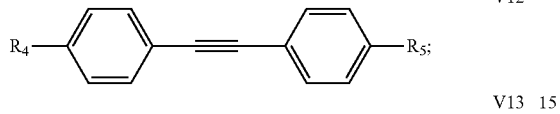
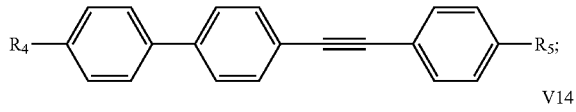
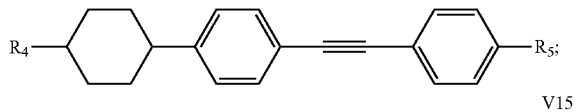
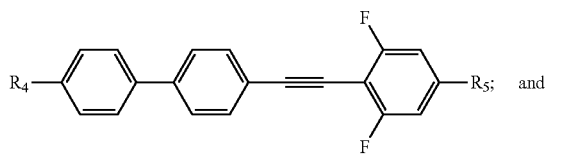
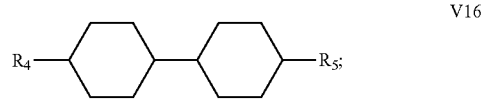

wherein:

$R_4$ and $R_5$ respectively and independently represent an alkyl group having 1-10 carbon atoms or an alkenyl group having 2-10 carbon atoms, in which any —$CH_2$— can be substituted by —$CH_2O$—, —$OCH_2$—, or —C≡C—, any H atom can be substituted by F; and (F) respectively and independently represents F or H.

An application of the above-described liquid crystal medium in preparation of a liquid crystal mixture, a material for a liquid crystal display device, or a material for an electro-optical display device also falls into the protection scope of the present invention.

The beneficial effects of the present invention are as follows:

Due to the existence of a rigid structure and two lateral fluorines in a molecule, the dibenzothiophene-class liquid crystals have a negative dielectric constant of a relatively large value. However, the existence of the rigid structure results in relatively poor solubility of this kind of compounds, thereby limiting applications thereof. It is surprising that, when one of a cyclopropyl group, a cyclopentyl group, and a 2-tetrahydrofuryl group is added in a molecule of the dibenzothiophene-class liquid crystals as a chain end group, The obtained liquid crystal compound has better intersolubility than this kind of traditional liquid crystal compounds containing a flexible alkyl chain. Therefore, the compound of formula I provided by the present invention can improve intersolubility of the liquid crystal compounds, thereby improving low temperature stability of a liquid crystal mixture and expanding an application range of the liquid crystal mixture; and the compound thus has an important application value.

BRIEF DESCRIPTION OF THE DRAWINGS

The specific embodiments of the present invention are further described below with reference to the drawings.

FIG. 1 shows a mass spectrogram of a compound of formula I12-2 according to embodiment 4.

DETAILED DESCRIPTION OF THE EMBODIMENTS

In order to more clearly describe the present invention, the present invention is further described below with reference to the preferred embodiments and the drawings. The similar components in the drawings are represented by the same drawing number. A person skilled in the art should understand that the following specific description content is for description instead of for limitation, and the protection scope of the present invention shall not limited thereto.

In the present invention, all the preparation methods, if not specifically described, are conventional methods; all the used raw materials, if not specifically described, can be obtained via a public commercial approach; and all the percentages, if not specifically described, are mass percentages.

In the present invention, a specific meaning of each symbol and a test condition are as follows:

GC represents gas chromatographic purity, MP represents a melting point, CP represents a clearing point, MS represents a mass spectrum, Δε represents dielectric anisotropy, and Δn represents optical anisotropy.

Methods for measuring GC, MP, CP, MS, Δε, and Δn are all conventional methods.

Embodiment 1

For a compound of which a structural formula is formula I1-1:

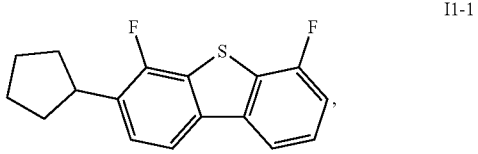 [SMILES: Fc1cccc2c1sc1c(F)c(C3CCCC3)ccc12]

a preparation method thereof is as follows.

Step 1:

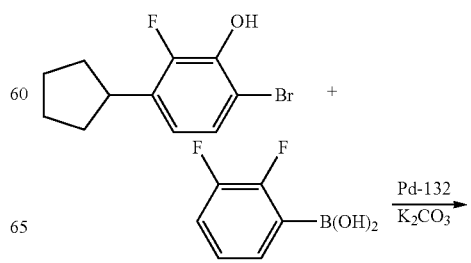

-continued

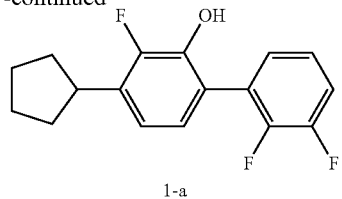

1-a 36.3 g (0.14 mol) of 2-fluoro-6-bromo-3-cyclopentylphenol, 22.6 g (0.14 mol) of 2,3-difluorophenylboronic acid, 43 g (0.31 mol) of potassium carbonate, 300 ml of methylbenzene, and 100 ml of pure water are added into a 1 L three-necked flask and mixed for total dissolution, 0.05 g of Pd-132 is added under the protection of nitrogen, and the mixture is heated at reflux for 6 h; after the reaction stops, 400 ml of pure water is added to and mixed with the mixture for liquid separation, a water layer is extracted by using 200 ml×2 of methylbenzene, organic layers are merged and washed by using 400 ml×2 of saturated salt solution, a solvent is spin-dried in reduced pressure, 80 g of petroleum ether is added to and mixed well with an obtained liquid, and recrystallization is performed in a temperature of −20° C. to obtain a white solid (1-a) with a mass of 33 g, GC of 98.5%, and a yield coefficient of 80.6%.

Step 2:

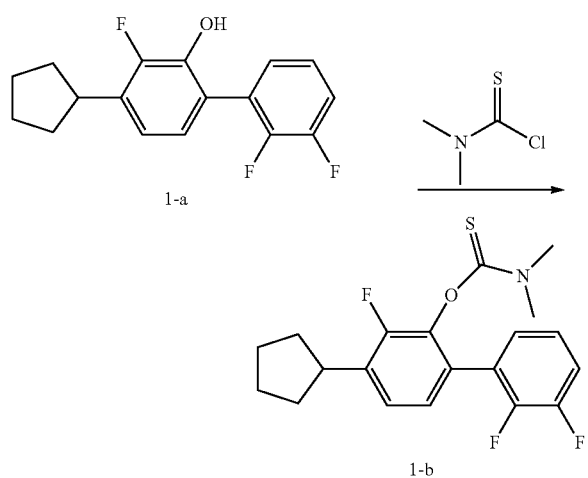

33 g (0.11 mol) of (1-a), 21.5 g (0.17 mol) of Dimethylcarbamothioic chloride, 22.2 g (0.22 mol) of triethylamine, and 300 ml of dichloromethane are added into a 1 L three-necked flask and mixed for 6 h in a room temperature for a reaction; after the reaction stops, 400 ml of pure water is added to and mixed with the mixture for liquid separation, a water layer is extracted by using 200 ml×2 of dichloromethane, organic layers are merged and washed by using 400 ml×2 of saturated sodium bicarbonate solution, a solvent is spin-dried in reduced pressure after being dried by using anhydrous sodium sulfate, 100 g of petroleum ether is added to and mixed well with an obtained liquid, and recrystallization is performed in a temperature of −20° C. to obtain a white solid (1-b) with a mass of 35 g, GC of 98.0%, and a yield coefficient of 83%.

Step 3:

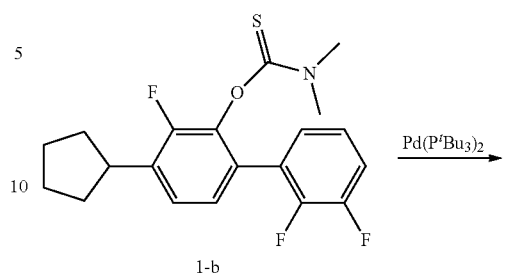

35 g (0.092 mol) of (1-b) and 300 ml of methylbenzene are added into a 1 L three-necked flask and mixed for total dissolution. 0.94 g of Pd(PtBu$_3$)$_2$ is added under the protection of nitrogen, and the mixture is heated to 100° C. for a reaction of 4 h; after the reaction stops, 400 ml of pure water is added to and mixed with the mixture for liquid separation, a water layer is extracted by using 200 ml×2 of methylbenzene, organic layers are merged and washed by using 400 ml×2 of saturated salt solution, a solvent is spin-dried in reduced pressure, 100 g of petroleum ether is added to and mixed well with an obtained liquid, and recrystallization is performed in a temperature of −20° C. to obtain a white solid (1-c) with a mass of 30 g, GC of 99.1%, and a yield coefficient of 86%.

Step 4:

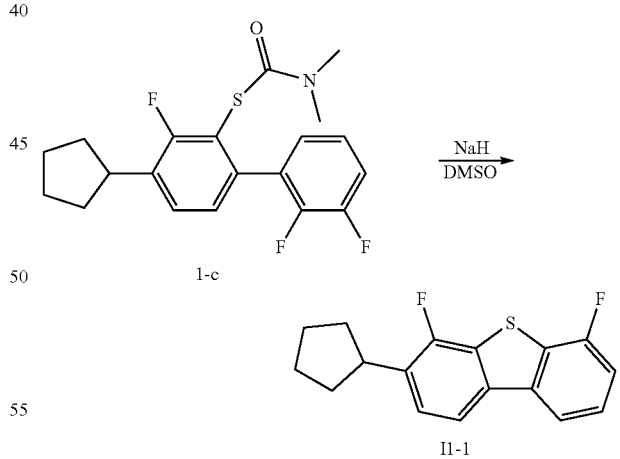

30 g (0.08 mol) of (1-c) is added into a 500 ml three-necked flask, 200 ml of dimethyl sulfoxide (DMSO) is added under the protection of nitrogen for well mixing, 8.8 g (0.22 mol) of 60% sodium hydride mineral oil is added, and the mixture is heated to 100° C. for stirring of 4 h; after the reaction stops, the mixture is cooled to a room temperature, a reaction liquid is poured into 300 g of ice water for stirring to separate out a large amount of solids, suction filtration is performed by using a filter cloth to obtain a solid, the solid is aired and heated to total dissolution after 200 ml of petroleum ether is added thereto, then chromatography with 30 g of hot silica column is performed, the column is flushed by using 200 ml of hot petroleum ether, a solution is spin-dried, methylbenzene and petroleum ether of the same amount with the solution are added for heating to total dissolution, and recrystallization is performed for two times in a temperature of 0° C. to obtain a white solid (I1-1) with a mass of 15 g, GC of 99.92%, and a yield coefficient of 65%.

Embodiment 2

For a compound of which a structural formula is formula 16-2:

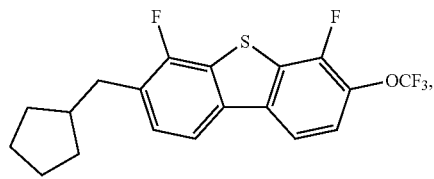 [SMILES: Fc1c(CC2CCCC2)ccc2c1sc1c(F)c(OC(F)(F)F)ccc12]
(I6-2)

a preparation route thereof is as follows.

Step 1:

a compound of the following formula 2-a is synthesized by using 2-fluoro-6-bromo-3-cyclopentylphenol and 2,3-difluoro-4-trifluoromethoxyphenylboronic acid as raw materials with reference to step 1 in embodiment 1:

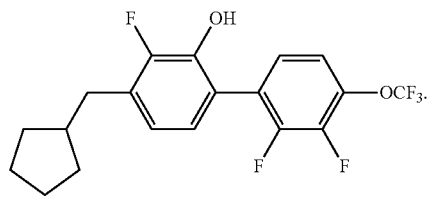
(2-a)

Step 2:

a compound of the following formula 2-b is synthesized by using the compound 2-a as a raw material with reference to the synthetic method in step 2 in embodiment 1:

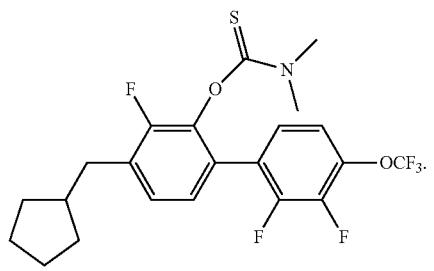
(2-b)

Step 3:

a compound of the following formula 2-c is synthesized by using the compound 2-b as a raw material with reference to step 3 in embodiment 1:

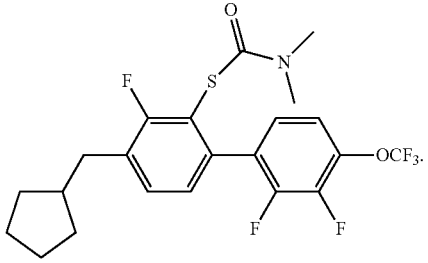
(2-c)

Step 4:

the target compound, that is, the compound of which the structural formula is formula 16-2 is synthesized by using the compound 2-c as a raw material with reference to step 4 in embodiment 1:

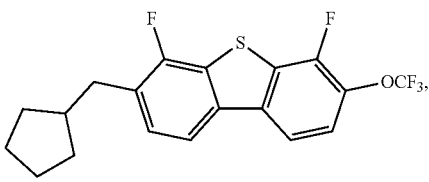

Embodiment 3

For a compound of which a structural formula is the following formula I12-1:

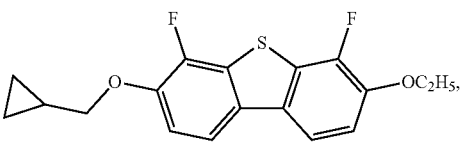 [SMILES: CCOc1ccc2c(sc3c(F)c(OCC4CC4)ccc32)c1F]

a preparation route thereof is as follows.

Step 1:

a compound of the following formula 3-a is synthesized by using 2-fluoro-6-bromo-3-cyclopropylmethoxyphenol and 2,3-difluoro-4-ethoxylphenylboronic acid as raw materials with reference to step 1 in embodiment 1:

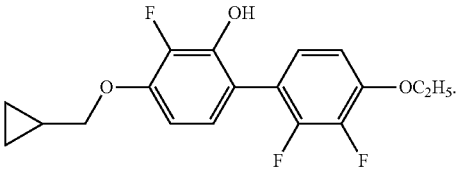
(3-a)

Step 2:

a compound of the following formula 3-b is synthesized by using the compound 3-a as a raw material with reference to the synthetic method in step 2 in embodiment 1:

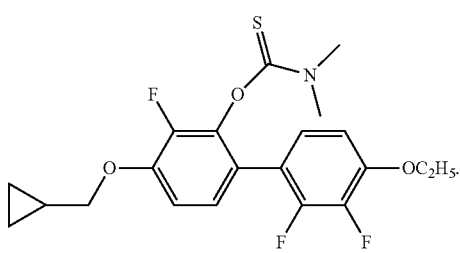
(3-b)

Step 3:

a compound of the following formula 3-c is synthesized by using the compound 3-b as a raw material with reference to step 3 in embodiment 1:

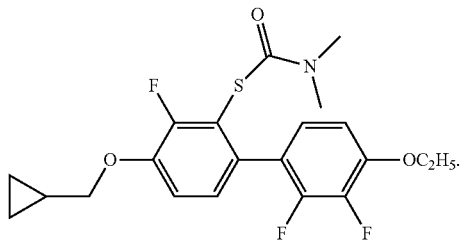
(3-c)

Step 4:

the target compound, that is, the compound of which the structural formula is formula. I12-1 is synthesized by using the compound 3-c as a raw material with reference to step 4 in embodiment 1:

Embodiment 4

For a compound of which a structural formula is the following formula I12-2:

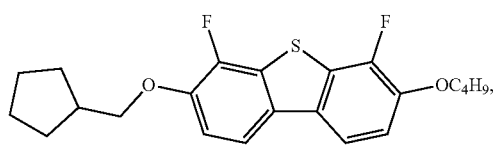

a preparation route thereof is as follows.

Step 1:

a compound of the following formula 4-a is synthesized by using 2-fluoro-6-bromo-3-cyclopentylmethoxyphenol and 2,3-difluoro-4-butoxyphenylboronic acid as raw materials with reference to step 1 in embodiment 1:

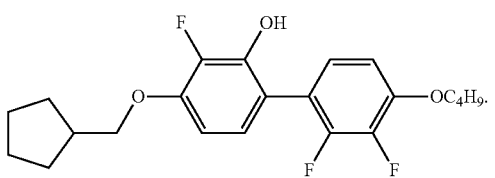
(4-a)

Step 2:

a compound of the following formula 4-b is synthesized by using the compound 4-a as a raw material with reference to the synthetic method in step 2 in embodiment 1:

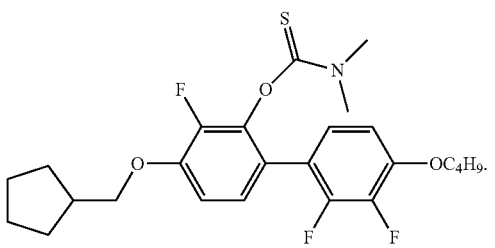
(4-b)

Step 3:

a compound of the following formula 4-c is synthesized by using the compound 4-b as a raw material with reference to step 3 in embodiment 1:

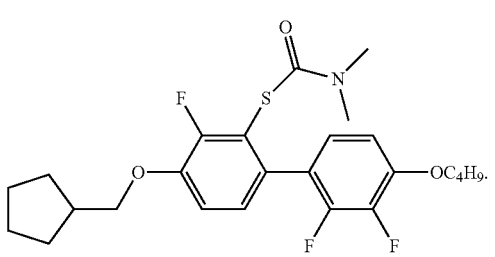
(4-c)

Step 4:

the target compound, that is, the compound of which the structural formula is formula I12-2 is synthesized by using the compound 4-c as a raw material with reference to step 4 in embodiment 1:

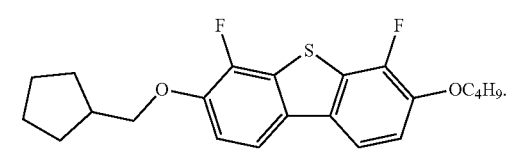

A spectrum of the obtained compound of formula I12-2 is as shown in FIG. 1.

Embodiment 5

For a compound of which a structural formula is the following formula I15-2:

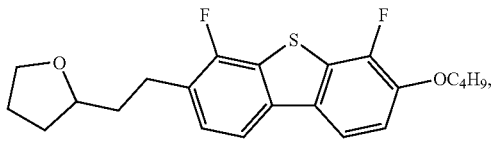

a preparation route thereof is as follows.

Step 1:

a compound of the following formula 5-a is synthesized by using 2-fluoro-6-bromo-3-(2-tetrahydrofuran)ethylphenol and 2,3-difluoro-4-butoxyphenylboronic acid as raw materials with reference to step 1 in embodiment 1:

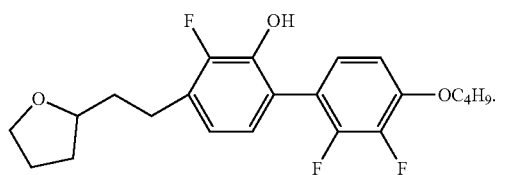

(5-a)

Step 2:

a compound of the following formula 5-b is synthesized by using the compound 5-a as a raw material with reference to the synthetic method in step 2 in embodiment 1:

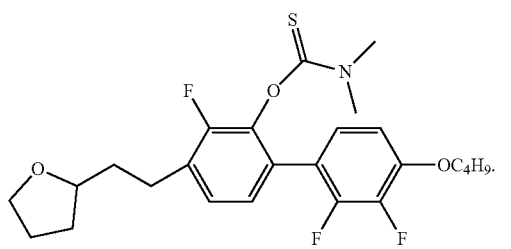

(5-b)

Step 3:

a compound of the following formula 5-c is synthesized by using the compound 5-b as a raw material with reference to step 3 in embodiment 1:

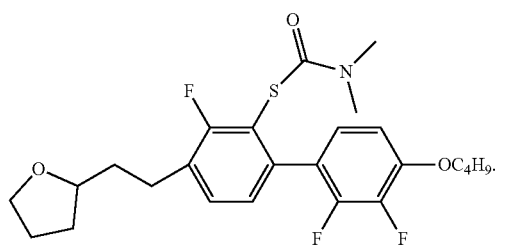

(5-c)

Step 4:

the target compound, that is, the compound of which the structural formula is formula I15-2 is synthesized by using the compound 5-c as a raw material with reference to step 4 in embodiment 1:

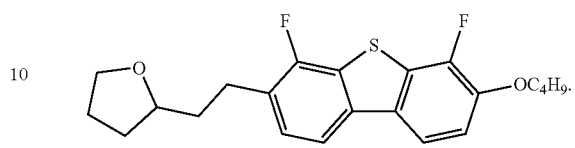

Mixture Embodiment

Embodiments 6-13

Embodiments 6-13 list preparation methods of different liquid crystal mediums, wherein a monomer structure and a dosage (weight percentage) of a specific compound in each embodiment, and a performance parameter test result of an obtained liquid crystal medium are respectively as shown in the following tables 1-8.

The temperature unit involved in each embodiment is ° C. and specific meanings and test conditions of other symbols are as follows:

S—N represents a melting point (° C.) for converting a liquid crystal from a crystalline state to a nematic phase;

c.p. represents a clearing point (° C.) of the liquid crystal, wherein a test instrument is: Mettler-Toledo-FP System micro-thermal analyzer;

$\gamma_1$ is rotational viscosity (mPa·s), wherein a test condition is as follows: 25° C., INSTEC: ALCT-IR1, and an 18-micrometer vertical box;

$K_{11}$ is twist elastic constant, $K_{33}$ is a splay elastic constant, wherein a test condition is as follows: 25° C. INSTEC: ALCT-IR1, and an 18-micrometer vertical box;

$\Delta\varepsilon$ represents dielectric anisotropy, $\Delta\varepsilon = \varepsilon_{//} 31 \ \varepsilon_\perp$ $^{\Delta\varepsilon=\varepsilon_{//}-\varepsilon_\perp}$, wherein $\varepsilon_{//}$ is a dielectric constant of a direction parallel to a molecular axis, $\varepsilon_\perp$ is a dielectric constant of a direction perpendicular to the molecular axis, and a test condition is as follows: 25° C., INSTEC: ALCT-IR1, and an 18-micrometer vertical box;

$\Delta n$ represents optical anisotropy, $\Delta n = n_o - n_e$, wherein $n_o$ is an ordinary Refractive index, $n_e$ is an extraordinary refractive index, and a test condition is as follows: 589 nm, and 25±0.2° C.

In the present invention, compounds of formulas I, IV, and V are respectively and proportionally weighed out to prepare the liquid crystal medium, wherein devices and instruments used for the preparation of the liquid crystal medium are as follows:

(1) an electronic precision balance (with accuracy of 0.1 mg);

(2) a stainless steel beaker: used to weigh out a compound raw material;

(3) a spoon: used to add a raw material;

(4) a magnetic rotor: used for stirring;

(5) a temperature-controlling electromagnetic stirrer.

The preparation method of the liquid crystal medium includes the following steps:

(1) the used raw materials are arranged orderly;

(2) the stainless steel beaker is placed on the balance, and the compound of formula I is put into the stainless steel beaker by using the spoon;

(3) other compound raw materials are sequentially added according to required weights thereof;

(4) the stainless steel beaker which all of the materials are added is placed on the magnetic stirring instrument and heated to melt the mixture; and (5) after most of the mixture in the stainless steel beaker is melted, one magnetic rotor is added into the stainless steel beaker to stir the liquid crystal mixture for well mixing, and the liquid crystal medium is obtained after the mixture is cooled to a room temperature.

The obtained liquid crystal medium are applied between two substrates of a liquid crystal display for performance test.

TABLE 1

Component proportion and performance parameter of the liquid crystal medium in embodiment 6

| Compound general formula | Liquid crystal structural formula | Weight percentage (%) | Performance parameter |
|---|---|---|---|
| V | $C_3H_7$—⬡—⬢—$OC_2H_5$ | 8 | S-N: ≤−40° C.; c.p: 80° C.; $\gamma_1$: 110 mPa · s; |
| V | $C_3H_7$—⬡—⬡—$C_5H_{11}$ | 10 | $\Delta n$: 0.091; $n_e$: 1.573; $\Delta\varepsilon$: −4.3; |
| V | $C_3H_7$—⬡—⬡—$C_2H_5$ | 10 | $\varepsilon_\perp$: 8.3; $K_{11}/K_{33}$: 13.5/14.7; the liquid crystal medium |
| V | $C_2H_5$—⬡—⬢—$C_3H_7$ | 5 | does not crystallize after being placed in a temperature of −20° C. |
| IV | ⬡—⬢($F,F$)—$OC_2H_5$ | 9 | for 480 h. |
| IV | ⬡—⬢($F,F$)—$OC_4H_9$ | 9 | |
| IV | $C_2H_5$—⬡—⬡—⬢($F,F$)—$CH_3$ | 8 | |
| IV | $C_3H_7$—⬡—⬡—⬢($F,F$)—$CH_3$ | 4 | |
| IV | $C_3H_7$—⬡—⬡—⬢($F,F$)—$OC_2H_5$ | 3 | |
| IV | $C_2H_5$—⬡—⬡—⬢($F,F$)—$OC_2H_5$ | 5 | |

TABLE 1-continued

Component proportion and performance parameter of the liquid crystal medium in embodiment 6

| Compound general formula | Liquid crystal structural formula | Weight percentage (%) | Performance parameter |
|---|---|---|---|
| IV | C$_4$H$_9$—[cyclohexyl]—[phenyl]—[difluoronaphthyl with F]—OC$_2$H$_5$ | 5 | |
| IV | C$_2$H$_5$—[cyclohexyl]—[phenyl]—[difluorophenyl]—OC$_2$H$_5$ | 10 | |
| IV | C$_3$H$_7$—[cyclohexyl]—[difluorophenyl]—C$_2$H$_4$—[difluorophenyl]—OC$_2$H$_5$ | 2 | |
| I | [cyclopentyl]—[difluorodibenzothiophene] | 5 | |
| I | [cyclopentyl]—CH$_2$—O—[difluorodibenzothiophene]—OC$_4$H$_9$ | 7 | |

TABLE 2

Component proportion and performance parameter of the liquid crystal medium in embodiment 7

| Compound general formula | Liquid crystal structural formula | Weight percentage (%) | Performance parameter |
|---|---|---|---|
| V | C$_3$H$_7$—[cyclohexyl]—[cyclohexyl]—vinyl | 38 | S-N: ≤−40° C.; c.p: 80° C.; γ$_1$: 90 mPa · s; |
| V | vinyl—[cyclohexyl]—[cyclohexyl]—[phenyl]—CH$_3$ | 3 | Δn: 0.100; n$_e$: 1.579; Δε: −3.8; |
| IV | [cyclohexyl]—CH$_2$O—[difluorophenyl]—OC$_2$H$_5$ | 5 | ε$_⊥$: 8.0; K$_{11}$/K$_{33}$: 14.5/16.0; the liquid crystal medium does not crystallize |
| IV | [cyclohexyl]—CH$_2$O—[difluorophenyl]—OC$_2$H$_5$ | 8 | after being placed in a temperature of −20° C. for 480 h. |

TABLE 2-continued

Component proportion and performance parameter of the liquid crystal medium in embodiment 7

| Compound general formula | Liquid crystal structural formula | Weight percentage (%) | Performance parameter |
|---|---|---|---|
| IV | [structure: propyl-cyclohexyl-cyclohexyl-CH₂O-difluorophenyl-OC₂H₅] | 10 | |
| IV | [structure: ethyl-cyclohexyl-cyclohexyl-CH₂O-difluorophenyl-OC₂H₅] | 10 | |
| IV | [structure: C₃H₇-cyclohexyl-phenyl-difluorophenyl-OC₂H₅] | 11 | |
| IV | [structure: C₅H₁₁-phenyl-phenyl-difluorophenyl-OC₂H₅] | 6 | |
| I | [structure: cyclopentylmethyl-difluorodibenzothiophene-OCF₃] | 4 | |
| I | [structure: cyclopentyl-difluorodibenzothiophene] | 5 | |

TABLE 3

Component proportion and performance parameter of the liquid crystal medium in embodiment 8

| Compound general formula | Liquid crystal structural formula | Weight percentage (%) | Performance parameter |
|---|---|---|---|
| V | [structure: C₃H₇-cyclohexyl-cyclohexyl-C₂H₅] | 12 | S-N: ≤−40° C.; c.p: 90° C.; $\gamma_1$: 134 mPa · s; |
| V | [structure: C₃H₇-cyclohexyl-cyclohexyl-C₅H₁₁] | 10 | Δn: 0.150; $n_e$: 1.640; Δε: −4.5; |
| V | [structure: C₃H₇-cyclohexyl-cyclohexyl-phenyl-C₃H₇] | 3 | $\varepsilon_\perp$: 8.5; $K_{11}/K_{33}$: 14.2/14.8; the liquid crystal |

TABLE 3-continued

Component proportion and performance parameter of the liquid crystal medium in embodiment 8

| Compound general formula | Liquid crystal structural formula | Weight percentage (%) | Performance parameter |
|---|---|---|---|
| V | C$_3$H$_7$—[Cy]—[Ph]—C≡C—[Ph]—C$_5$H$_{11}$ | 5 | medium does not crystallize after being placed |
| IV | Et—[Cy]—[Ph(F,F)]—C≡C—[Ph(F,F)]—OC$_2$H$_5$ | 3 | in a temperature of −20° C. for 480 h. |
| IV | C$_5$H$_{11}$—[Cy]—[Cy]—[Ph(F,F)]—OC$_2$H$_5$ | 9 | |
| IV | C$_3$H$_7$—[Cy]—[Ph]—[Ph(F,F)]—OC$_2$H$_5$ | 6 | |
| IV | C$_5$H$_{11}$—[Ph]—[Ph]—[Ph(F,F)]—OC$_2$H$_5$ | 3 | |
| IV | C$_5$H$_{11}$—[Ph]—[Ph]—[Ph(F,F)]—OC$_2$H$_5$ | 5 | |
| IV | Pr—[Ph]—C≡C—[Ph(F,F)]—OEt | 15 | |
| IV | Pr—[Ph(F,F)]—C≡C—[Ph(F,F)]—OEt | 13 | |
| I | cyclopropyl-CH$_2$CH$_2$—[dibenzothiophene(F,F)]—OC$_2$H$_5$ | 6 | |
| I | cyclopentyl—[dibenzothiophene(F,F)] | 10 | |

TABLE 4

Component proportion and performance parameter of the liquid crystal medium in embodiment 9

| Compound general formula | Liquid crystal structural formula | Weight percentage (%) | Performance parameter |
|---|---|---|---|
| V | 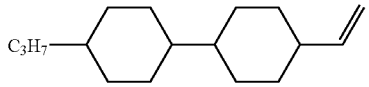 | 17 | S-N: ≤−40° C.; c.p: 100° C.; γ₁: 140 mPa · s; |
| V | 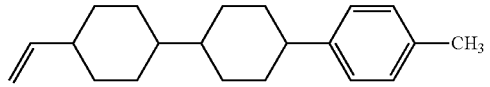 [SMILES: C=CC1CCC(C2CCC(c3ccc(C)cc3)CC2)CC1] | 12 | Δn: 0.105; $n_e$: 1.594; Δε: −3.6; |
| V |  | 4 | $\varepsilon_\perp$: 7.4; $K_{11}/K_{33}$: 15.5/18.0; the liquid crystal |
| V | 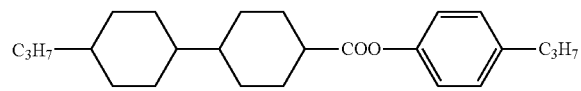 | 3 | medium does not crystallize after being placed |
| V | 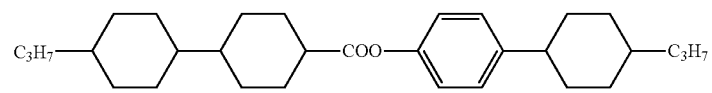 | 5 | in a temperature of −20° C. for 480 h. |
| IV | 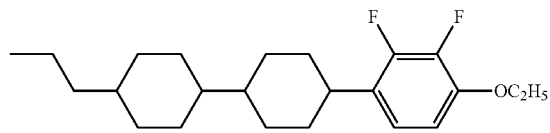 [SMILES: CCCC1CCC(C2CCC(c3ccc(OCC)c(F)c3F)CC2)CC1] | 5 | |
| IV | 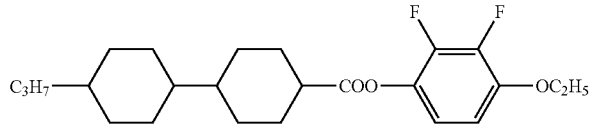 | 4 | |
| IV | 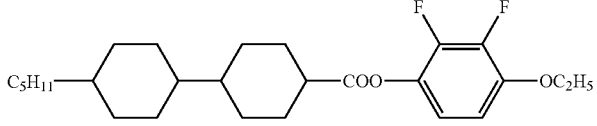 | 4 | |
| IV | 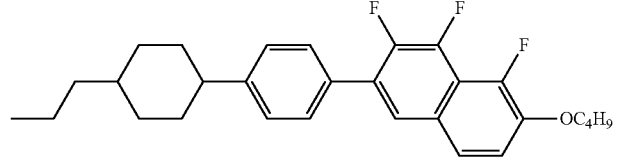 | 8 | |
| IV | 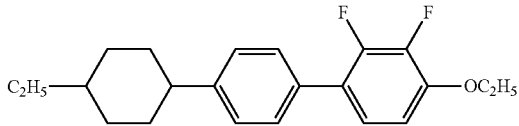 | 8 | |
| IV | 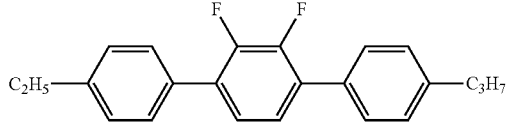 | 5 | |

TABLE 4-continued

Component proportion and performance parameter of the liquid crystal medium in embodiment 9

| Compound general formula | Liquid crystal structural formula | Weight percentage (%) | Performance parameter |
|---|---|---|---|
| IV | [propyl-cyclohexyl-naphthalene with F,F,F substituents and -OC$_2$H$_5$] | 12 | |
| IV | [C$_3$H$_7$-cyclohexyl-phenyl with F,F and -OC$_4$H$_9$] | 12 | |
| I | [cyclopentylmethyl-O-dibenzothiophene with F,F and -OC$_4$H$_9$] | 1 | |

TABLE 5

Component proportion and performance parameter of the liquid crystal medium in embodiment 10

| Compound general formula | Liquid crystal structural formula | Weight percentage (%) | Performance parameter |
|---|---|---|---|
| V | [C$_3$H$_7$-cyclohexyl-cyclohexyl-vinyl] | 14 | S-N: ≤−40° C.; c.p: 78° C.; $\gamma_1$: 89 Pa·s; |
| V | [vinyl-cyclohexyl-cyclohexyl-phenyl-CH$_3$] | 7 | $\Delta n$: 0.106; $n_e$: 1.595; $\Delta\varepsilon$: −3.6; |
| V | [C$_3$H$_7$-cyclohexyl-phenyl-phenyl-C$_3$H$_7$] | 3 | $\varepsilon_\perp$: 7.4; $K_{11}/K_{33}$: 13.2/13.5; the liquid crystal |
| V | [C$_3$H$_7$-cyclohexyl-phenyl-OC$_2$H$_5$] | 8 | medium does not crystallize after being placed |
| V | [C$_3$H$_7$-cyclohexyl-cyclohexyl-C$_2$H$_5$] | 7 | in a temperature of −20° C. for 480 h. |
| V | [C$_3$H$_7$-cyclohexyl-cyclohexyl-propenyl] | 7 | |
| IV | [C$_3$H$_7$-cyclohexyl-cyclohexyl-naphthalene with F,F,F and -CH$_3$] | 5 | |

TABLE 5-continued

Component proportion and performance parameter of the liquid crystal medium in embodiment 10

| Compound general formula | Liquid crystal structural formula | Weight percentage (%) | Performance parameter |
|---|---|---|---|
| IV | C₅H₁₁–[Cy]–[Cy]–[Ph(2,3-F₂)]–OC₂H₅ | 5 | |
| IV | C₂H₅–[Cy]–[Ph]–[Ph(2,3-F₂)]–OC₂H₅ | 9 | |
| IV | C₂H₅–[Ph]–[Ph(2,3-F₂)]–[Ph]–C₃H₇ | 5 | |
| IV | C₃H₇–[Cy]–[Naphthalene(F₃)]–OC₂H₅ | 10 | |
| IV | C₃H₇–[Ph]–[Naphthalene(F₃)]–OC₂H₅ | 10 | |
| IV | C₃H₇–[Cy]–[Ph(2,3-F₂)]–C₂H₄–[Ph(2,3-F₂)]–OC₂H₅ | 5 | |
| I | cyclopentyl-CH₂-O–[dibenzothiophene(F₂)]–OC₄H₉ | 5 | |

TABLE 6

Component proportion and performance parameter of the liquid crystal medium in embodiment 11

| Compound general formula | Liquid crystal structural formula | Weight percentage (%) | Performance parameter |
|---|---|---|---|
| V | C₃H₇–[Cy]–[Cy]–CH=CH₂ | 14 | S-N: ≤−40° C.; c.p: 77° C.; $\gamma_1$: 88 Pa · s; |
| V | CH₂=CH–[Cy]–[Cy]–[Ph]–CH₃ | 7 | $\Delta n$: 0.104; $n_e$: 1.587; $\Delta\varepsilon$: −3.7; |

TABLE 6-continued

Component proportion and performance parameter of the liquid crystal medium in embodiment 11

| Compound general formula | Liquid crystal structural formula | Weight percentage (%) | Performance parameter |
|---|---|---|---|
| V |  | 3 | $\varepsilon_\perp$: 7.6; $K_{11}/K_{33}$: 13.7/13.9; the liquid crystal medium does not crystallize after being placed in a temperature of −20° C. for 480 h. |
| V | 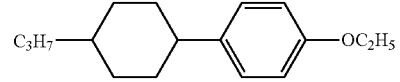 | 8 | |
| V | 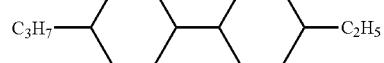 | 7 | |
| V | 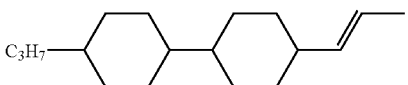 | 7 | |
| IV | 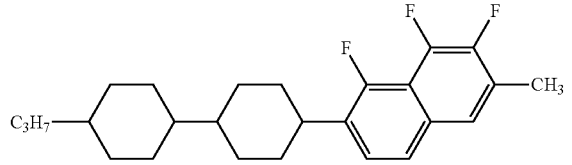 | 5 | |
| IV |  | 5 | |
| IV | 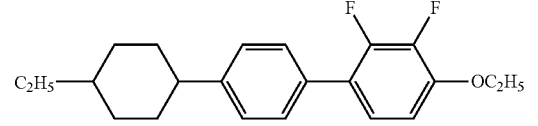 | 9 | |
| IV | 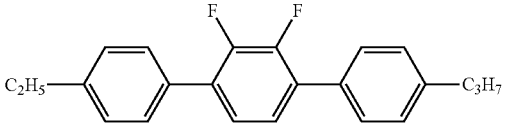 | 5 | |
| IV | 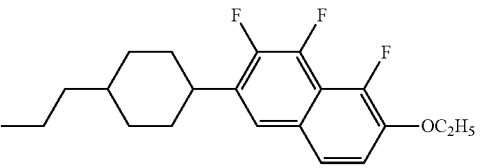 [SMILES: CCCC1CCC(c2cc3ccc(OCC)c(F)c3c(F)c2F)CC1] | 10 | |
| IV | 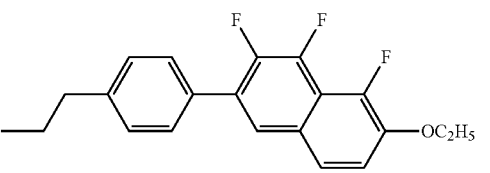 [SMILES: CCCc1ccc(-c2cc3ccc(OCC)c(F)c3c(F)c2F)cc1] | 10 | |
| IV | 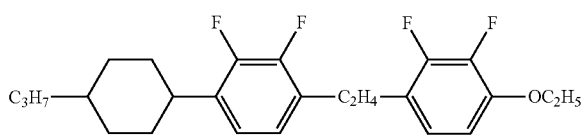 | 5 | |

TABLE 6-continued

Component proportion and performance parameter of the liquid crystal medium in embodiment 11

| Compound general formula | Liquid crystal structural formula | Weight percentage (%) | Performance parameter |
|---|---|---|---|
| I | cyclopropyl-CH$_2$-O-[3,4-difluorodibenzothiophene]-OC$_2$H$_5$ | 5 | |

TABLE 7

Component proportion and performance parameter of the liquid crystal medium in embodiment 12

| Compound general formula | Liquid crystal structural formula | Weight percentage (%) | Performance parameter |
|---|---|---|---|
| V | C$_3$H$_7$-Cy-Cy-CH=CH$_2$ | 32 | S-N: ≤−40° C.; c.p: 85° C.; γ$_1$: 145 mPa·s; |
| IV | C$_3$H$_7$-Cy-[2,3-difluorophenyl]-OC$_2$H$_5$ | 12 | Δn: 0.100; n$_e$: 1.582; Δε: −5.0; ε$_\perp$: 9.3; K$_{11}$/K$_{33}$: 14.5/16.5; |
| IV | C$_2$H$_5$-Cy-Ph-[2,3-difluorophenyl]-OC$_2$H$_5$ | 12 | the liquid crystal medium does not crystallize after being placed in a temperature of −20° C. for 480 h. |
| IV | C$_3$H$_7$-Cy-[2,3-difluorophenyl]-C$_2$H$_4$-[2,3-difluorophenyl]-OC$_2$H$_5$ | 8 | |
| IV | C$_3$H$_7$-Cy-Cy-COO-[2,3-difluorophenyl]-OC$_2$H$_5$ | 8 | |
| IV | C$_2$H$_5$O-[2,3-difluorophenyl]-Cy-Cy-CH=CH$_2$ | 8 | |
| IV | C$_2$H$_5$O-[2,3-difluorophenyl]-Cy-Cy-CH=CH-CH$_3$ | 8 | |
| I | cyclopentyl-CH$_2$-O-[3,4-difluorodibenzothiophene]-OC$_4$H$_9$ | 5 | |

TABLE 7-continued

Component proportion and performance parameter of the liquid crystal medium in embodiment 12

| Compound general formula | Liquid crystal structural formula | Weight percentage (%) | Performance parameter |
|---|---|---|---|
| I | 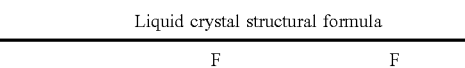 | 7 | |

TABLE 8

Component proportion and performance parameter of the liquid crystal medium in embodiment 13

| Compound general formula | Liquid crystal structural formula | Weight percentage (%) | Performance parameter |
|---|---|---|---|
| V | | 38 | S-N: ≤−40° C.; c.p: 75° C.; $\gamma_1$: 108 mPa · s; |
| V | | 3 | $\Delta n$: 0.100; $n_e$: 1.581; $\Delta \varepsilon$: −5.0; |
| IV | | 5 | $\varepsilon_\perp$: 9.3; $K_{11}/K_{33}$: 14.5/18.5; the liquid crystal medium does not crystallize |
| IV | | 8 | after being placed in a temperature of −20° C. for 480 h. |
| IV | | 10 | |
| IV | | 10 | |
| IV | | 6 | |
| IV | | 6 | |

TABLE 8-continued

Component proportion and performance parameter of the liquid crystal medium in embodiment 13

| Compound general formula | Liquid crystal structural formula | Weight percentage (%) | Performance parameter |
|---|---|---|---|
| I | 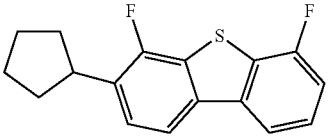 | 9 | |
| I | 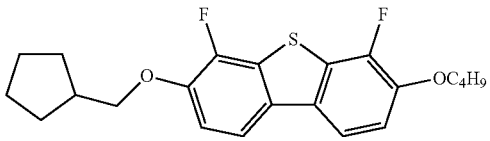 | 5 | |

Comparison Embodiment 1

A component is as shown in the following table 9, wherein components thereof include a compound of which a structural formula is formula VI but do not include the compound of which the structural formula is formula I.

Comparison Embodiment 2

A component is as shown in the following table 10, wherein the components thereof include a compound of which a structural formula is formula VII but do not include the compound of which the structural formula is formula I.

TABLE 9

Component proportion and performance parameter of the liquid crystal medium in embodiment 1

| Compound general formula | Liquid crystal structural formula | Weight percentage (%) | Performance parameter |
|---|---|---|---|
| V | 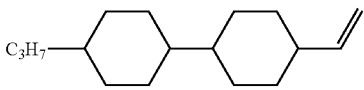 | 14 | S-N: ≤−20° C.; c.p: 70° C.; $\gamma_1$: 84 Pa · s; |
| V | 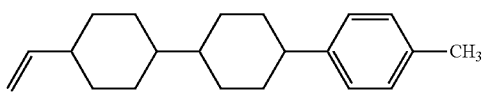 [SMILES: C=CC1CCC(C2CCC(c3ccc(C)cc3)CC2)CC1] | 7 | Δn: 0.100; $n_e$: 1.586; Δε: −3.2; |
| V |  | 3 | $\varepsilon_\perp$: 6.8; $K_{11}/K_{33}$: 12.3/12.8; the liquid crystal |
| V | 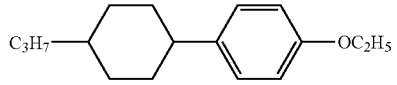 | 8 | medium crystallizes after being placed in a temperature |
| V | 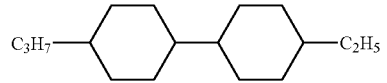 | 7 | of −20° C. for 240 h. |
| V | 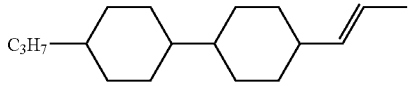 | 7 | |
| IV | 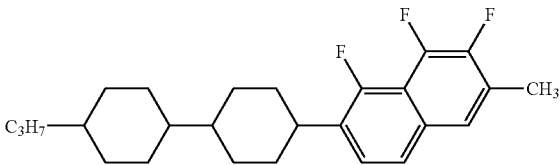 | 5 | |

TABLE 9-continued

Component proportion and performance parameter of the liquid crystal medium in embodiment 1

| Compound general formula | Liquid crystal structural formula | Weight percentage (%) | Performance parameter |
|---|---|---|---|
| IV | C₅H₁₁–cyclohexyl–cyclohexyl–(2,3-difluoro)phenyl–OC₂H₅ | 5 | |
| IV | C₂H₅–cyclohexyl–phenyl–(2,3-difluoro)phenyl–OC₂H₅ | 9 | |
| IV | C₂H₅–phenyl–(2,3-difluoro)phenyl–phenyl–C₃H₇ | 5 | |
| IV | propyl–cyclohexyl–(trifluoro)naphthyl–OC₂H₅ | 10 | |
| IV | propyl–phenyl–(trifluoro)naphthyl–OC₂H₅ | 10 | |
| IV | C₃H₇–cyclohexyl–(2,3-difluoro)phenyl–C₂H₄–(2,3-difluoro)phenyl–OC₂H₅ | 5 | |
| VI | C₅H₁₁O–(4,6-difluoro-dibenzothiophene)–OC₄H₉ | 5 | |

TABLE 10

Component proportion and performance parameter of the liquid crystal medium in embodiment 2

| Compound general formula | Liquid crystal structural formula | Weight percentage (%) | Performance parameter |
|---|---|---|---|
| V | C₃H₇–cyclohexyl–cyclohexyl–vinyl | 14 | S-N: ≤−20° C.; c.p: 71° C.; γ₁: 88 Pa·s; |
| V | vinyl–cyclohexyl–cyclohexyl–phenyl–CH₃ | 7 | Δn: 0.103; nₑ: 1.584; Δε: −3.3; |

TABLE 10-continued
Component proportion and performance parameter of the liquid crystal medium in embodiment 2
| Compound general formula | Liquid crystal structural formula | Weight percentage (%) | Performance parameter |
|---|---|---|---|
| V |  | 3 | $\varepsilon_\perp$: 6.7; $K_{11}/K_{33}$: 12.0/12.5; the liquid crystal medium crystallizes after being placed in a temperature of −20° C. for 240 h. |
| V | 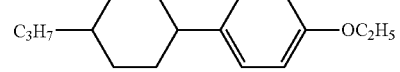 | 8 | |
| V | 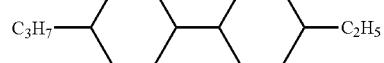 | 7 | |
| V | 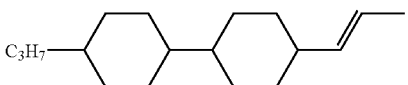 | 7 | |
| IV | 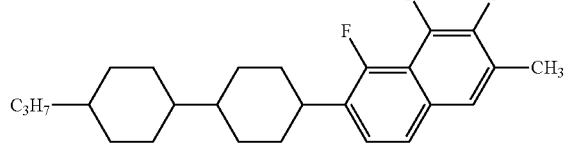 | 5 | |
| IV |  | 5 | |
| IV | 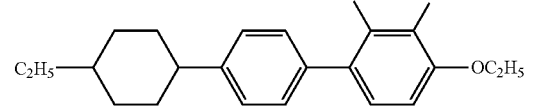 | 9 | |
| IV | 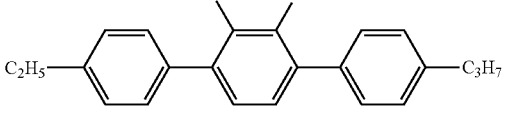 | 5 | |
| IV | 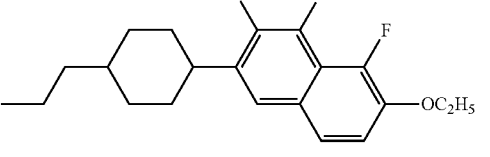 | 10 | |
| IV | 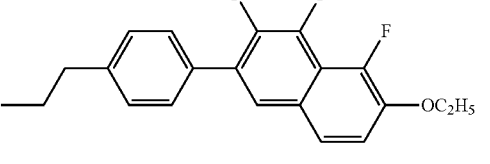 | 10 | |
| IV | 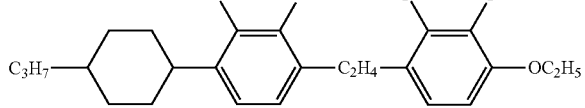 | 5 | |

TABLE 10-continued

Component proportion and performance parameter of the liquid crystal medium in embodiment 2

| Compound general formula | Liquid crystal structural formula | Weight percentage (%) | Performance parameter |
|---|---|---|---|
| VII | 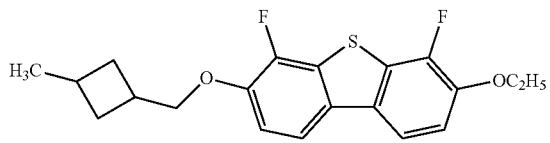 [SMILES: CCOc1ccc2c(sc3c(F)c(OCC4CC(C)C4)ccc32)c1F] | 5 | |

It can be known from the performance parameters of the liquid crystal compositions shown in embodiments 6-13 that, the liquid crystal compositions of the present invention have excellent intersolubility and a negative dielectric constant of an extremely large absolute value. In addition, it can be known from the comparisons of embodiment 10 with comparison embodiment 1 and comparison embodiment 2 that, dibenzothiophene-class liquid crystal compounds using a cyclopropyl group, a cyclopentyl group, and a 2-tetrahydrofuryl group as end groups have better intersolubility than traditional dibenzothiophene-class liquid crystals using a flexible alkyl chain as an end group, and low temperature stability thereof is correspondingly improved. Therefore, the compound of formula I provided by the present invention can improve intersolubility of the liquid crystal compounds, thereby expanding an application range of a liquid crystal mixture; and the compound thus has an important application value.

Although the present invention only lists out the specific compounds and proportion dosages thereof (weight percentage) of the above-described eight embodiments and the comparison embodiments thereof and the performance tests are performed, based on the above-described embodiments, the liquid crystal composition of the present invention can be further expanded and modified by using the liquid crystal compounds represented by formulas I, IV, and V involved in the present invention and preferred liquid crystal compounds of formulas I, IV, and V, and the objective of the present invention can be achieved by appropriately adjusting the proportion dosages thereof.

Apparently, the above-described embodiments of the present invention are merely illustrative for clear description of the present invention and are not intended to limit the embodiments of the present invention, and those skilled in the art could also make other changes or modifications of different forms on the basis of the above description. The changes and modifications of all of the embodiments are not exhaustive herein, and any obvious changes or modifications derived from the technical solutions of the present invention are still within the protection scope of the present invention.

The invention claimed is:

1. A liquid crystal medium containing one or more of the compounds having a following formula I:

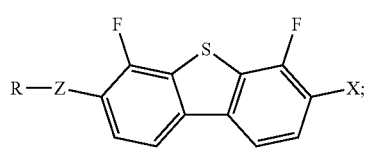

wherein:

R represents one of a cyclopropyl group, a cyclopentyl group, and a 2-tetrahydrofuryl group;

Z represents one of a single bond, —O—, —CH$_2$CH$_2$—, —CH$_2$O—, —CF$_2$O—, and —COO—; and X represents one of H, F, an alkyl group having 1-7 carbon atoms, and an alkoxygroup having 1-7 carbon atoms, wherein in the alkyl group having 1-7 carbon atoms and the alkoxygroup having 1-7 carbon atoms, one or more H atoms can be substituted by F, wherein the liquid crystal medium further comprises one or more compounds of the following formulas IV1 to IV15:

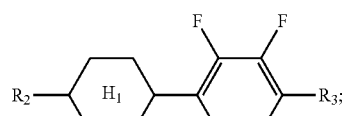

IV1

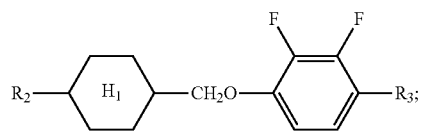

IV2

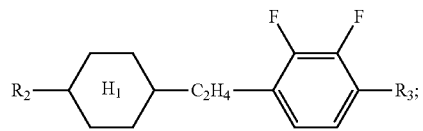

IV3

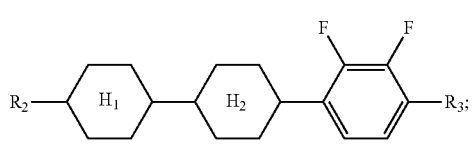

IV4

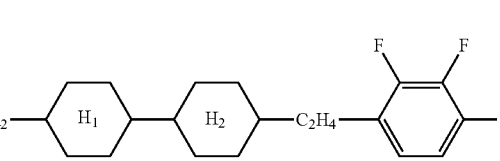

IV5

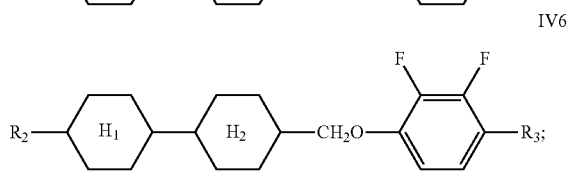

IV6

-continued

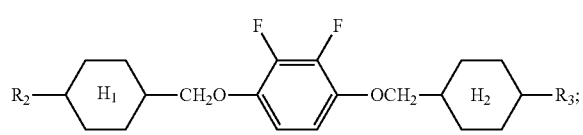
IV7

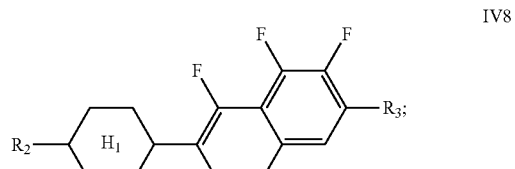
IV8

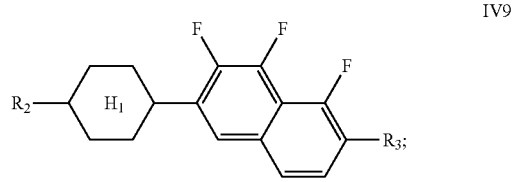
IV9

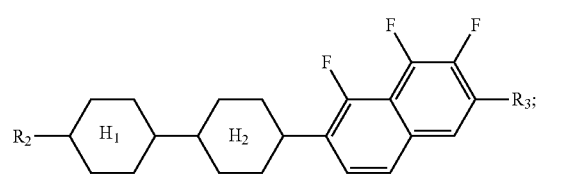
IV10

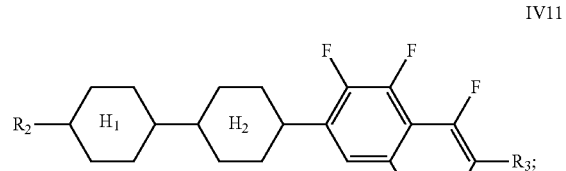
IV11

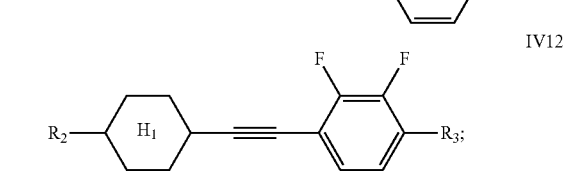
IV12

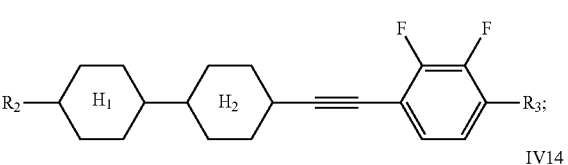
IV13

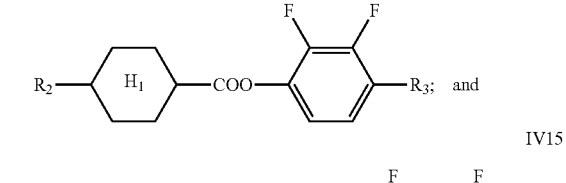
IV14

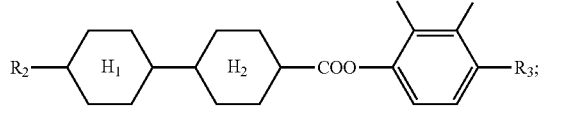
IV15 wherein:
R2 and R3 respectively and independently represent any one group in the following groups represented by (1)-(3):
(1) a linear alkyl group having 1-7 carbon atoms or a linear alkoxygroup having 1-7 carbon atoms;
(2) a group formed by substituting —O—, —COO—, —OOC—, or —CH=CH— for one or more —CH2— in anyone group represented by (1); and
(3) a group formed by substituting F, Cl, —CH=CH$_2$, or —CH=CH—CH$_3$ for one or more H atoms in anyone group represented by (1);

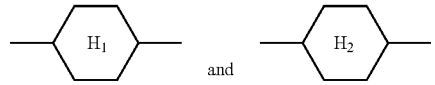

respectively and independently represent any one group in the following groups:

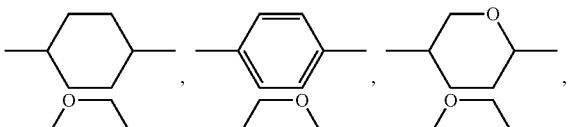

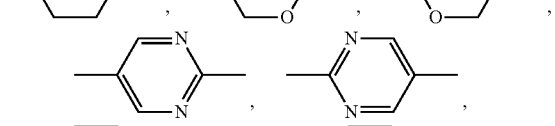

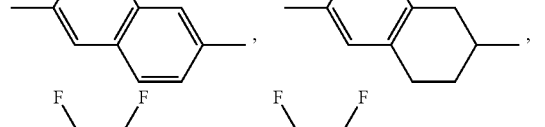

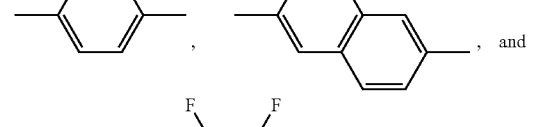

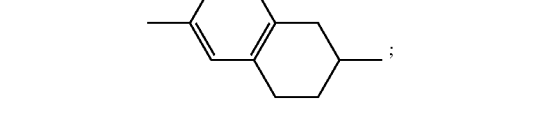

and
wherein in formula IV4,

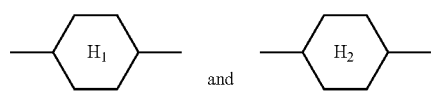

are not both

2. The liquid crystal medium according to claim 1, wherein the liquid crystal medium further comprises one or more compounds of which a structural formula is formula V:

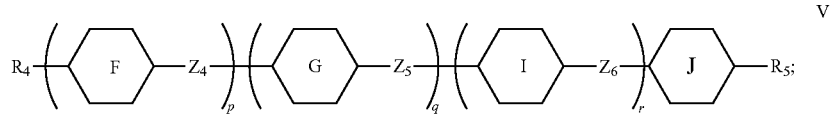

wherein:
R₄ and R₅ respectively and independently represent an alkyl group having 1-10 carbon atoms or an alkenyl group having 2-10 carbon atoms, in which any —CH₂— can be substituted by —CH₂O—, —OCH₂—, or —C≡C—, and any H atom can be substituted by F;

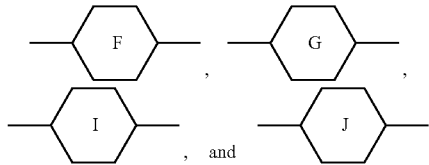

respectively and independently represent the following groups:

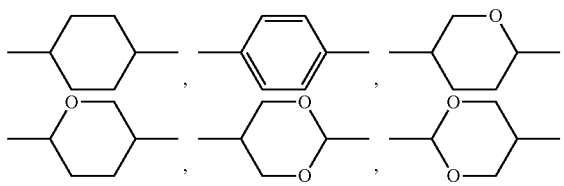

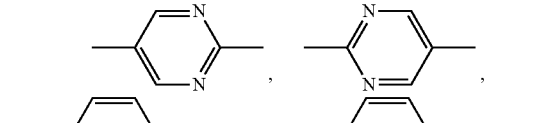

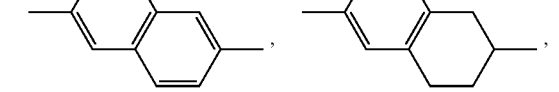

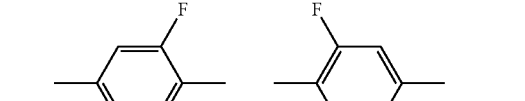

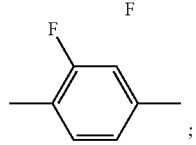

p, q, and r respectively and independently represent 0 or 1; and

Z₄, Z₅, and Z₆ respectively and independently represent one of a single bond, —C₂H₄—, —CH═CH—, —COO—, —OOC—, —CH₂O—, —OCH₂—, —CF₂O—, and —OCF₂—, in which any H atom can be substituted by F.

3. The liquid crystal medium according to claim 2, wherein in the liquid crystal medium, a mass percentage of the compound of which the structural formula is formula I being 1-24%, a mass percentage of the compound of which the structural formula is formula IV being 35-58%, and a mass percentage of the compound of which the structural formula is formula V being 30-46%.

4. The liquid crystal medium according to claim 2, wherein the structural formula of the compound of which the structural formula is formula V being specifically represented as the following formulas V1 to V16:

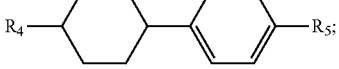

V1

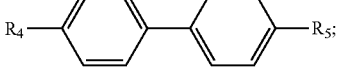

V2

V3

V4

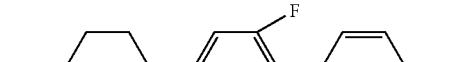

V5

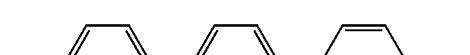

V6

V7

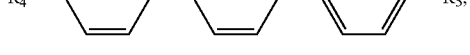

V8

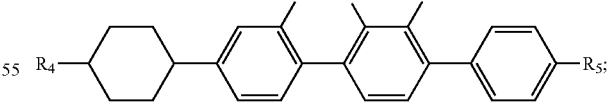

V9

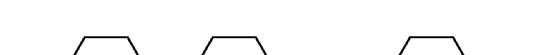

V10

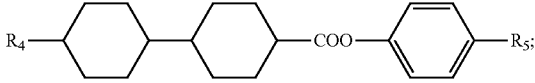

-continued

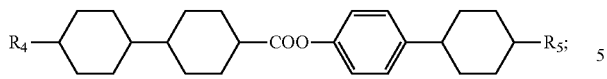
V11

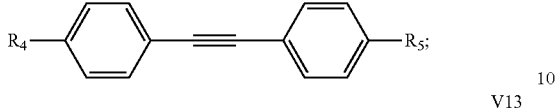
V12

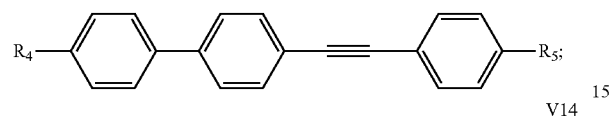
V13

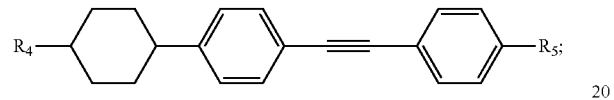
V14

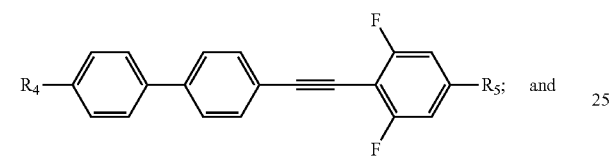
V15

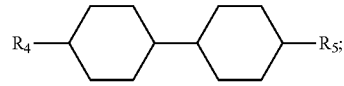
V16 wherein:

$R_4$ and $R_5$ respectively and independently represent an alkyl group having 1-10 carbon atoms or an alkenyl group having 2-10 carbon atoms, in which any —$CH_2$— can be substituted by —$CH_2O$—, —$OCH_2$—, or —C≡C—, any H atom can be substituted by F; and (F) respectively and independently represents F or H.

5. A liquid crystal display device comprising the liquid crystal medium according to claim 1.

6. The liquid crystal medium according to claim 3, wherein the structural formula of the compound of which the structural formula is formula V being specifically represented as the following formulas V1 to V16:

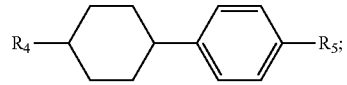
V1

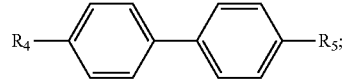
V2

V3

V4

-continued

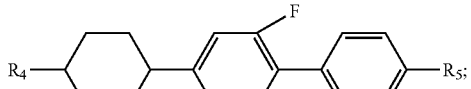
V5

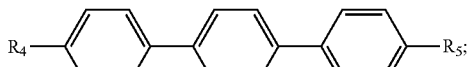
V6

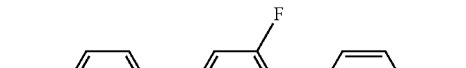
V7

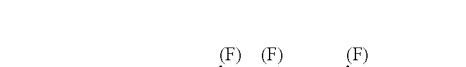
V8

V9

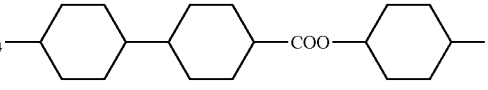
V10

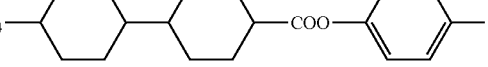
V11

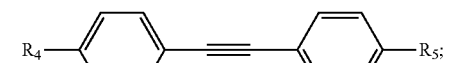
V12

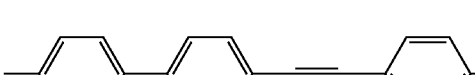
V13

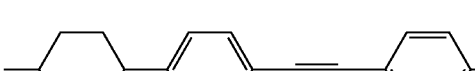
V14

V15

V16 wherein:

$R_4$ and $R_5$ respectively and independently represent an alkyl group having 1-10 carbon atoms or an alkenyl group having 2-10 carbon atoms, in which any —$CH_2$— can be substituted by —$CH_2O$—, —OCH₂—, or —C≡C—, any H atom can be substituted by F; and (F) respectively and independently represents F or H.

7. A method of preparing a liquid crystal mixture, a material for a liquid crystal display device, or a material for an electro-optical display device, the method comprising administering the liquid crystal medium according to claim 1.

8. A method of preparing a liquid crystal mixture, a material for a liquid crystal display device, or a material for an electro-optical display device, the method comprising administering the liquid crystal medium according to claim 2.

9. A method of preparing a liquid crystal mixture, a material for a liquid crystal display device, or a material for an electro-optical display device, the method comprising administering the liquid crystal medium according to claim 3.

10. A method of preparing a liquid crystal mixture, a material for a liquid crystal display device, or a material for an electro-optical display device, the method comprising administering the liquid crystal medium according to claim 4.

11. An electro-optical display device comprising the liquid crystal medium according to claim 1.

* * * * *